United States Patent [19]

Hachikubo et al.

[11] 4,059,488
[45] Nov. 22, 1977

[54] METHOD OF PRODUCING LONG-CHAIN ALPHA-HYDROXYALKANOIC ACIDS

[75] Inventors: Kazumasa Hachikubo, Toda; Shuzo Suzuki, Sayama, both of Japan

[73] Assignee: Bio Research Center, Co., Ltd., Tokyo, Japan

[21] Appl. No.: 693,852

[22] Filed: June 8, 1976

[30] Foreign Application Priority Data

June 20, 1975   Japan ................................. 50-76123

[51] Int. Cl.$^2$ ......................... C12D 1/02; C12K 3/00
[52] U.S. Cl. .................................. 195/28 R; 195/79; 195/82; 195/112
[58] Field of Search ................... 195/28 R, 82, 46, 76, 195/79, 112

[56] References Cited

U.S. PATENT DOCUMENTS 3,843,466   10/1974   Akabori et al. .................... 195/28 R

OTHER PUBLICATIONS

Klug et al., "Fermentation of 1-Hexadecene by Candida lipolytica", Chemical Abstracts, vol. 72, No. 1, p. 191, (1970), Abs. No. 2145m.

Jwanny et al., "Utilization of Hydrocarbons by Microorganisms, Biochemical Activities of Alkanes-grown Candida lipolytica," Chemical Abstracts, vol. 81, No. 1, (1974), p. 100, Abs. No. 1199f.

Nyns et al., "Adaptive or Constitutive Nature of the Enzymes Involved in the Oxidation of n-Hexadecane to Palmitive Acid by Candida Lipolytica", Chemical Abstracts, vol. 72, No. 9, (1970), p. 123, Abs. No. 40084y.

Mishina et al., "Effects of Chain-length Alkane Substrate on Fatty Acid Composition and Biosynthetic Pathway in Some Yeasts", Agr. Biol. Chem., vol. 37, No. 4, (1973), pp. 863-870.

Waddams, Chemicals From Petroleum, The Noyes Press, Inc., Pearl River, N.Y., (1962), p. 14.

Primary Examiner—Alvin E. Tanenholtz
Assistant Examiner—Thomas G. Wiseman
Attorney, Agent, or Firm—Donald R. Cassady; Meyer Neishloss

[57] ABSTRACT

Long-chain alpha-hydroxyalkanoic acids are prepared from alpha olefins having 10 to 18 carbon atoms by first adapting a microorganism of the Candida lipolytica species to assimilate the alpha olefins in such a way that the so-adapted microorganism produces as the major metabolite of said assimilation alpha-hydroxyalkanoic acids having the same number of carbon atoms as the alpha olefins when the adapted microorganism is cultivated in an aqueous nutrient medium containing the alpha olefins. The adaptation procedure comprises first cultivating the Candida lipolytica species in an aqueous nutrient medium containing kerosene boiling range hydrocarbons and then repetitively cultivating in a series of separate successive steps in an aqueous nutrient medium containing an alpha olefin the successive microorganism cultures obtained in the preceding cultivation steps beginning with the culture obtained using the kerosene hydrocarbons as the carbon source.

3 Claims, No Drawings

METHOD OF PRODUCING LONG-CHAIN ALPHA-HYDROXYALKANOIC ACIDS

BACKGROUND OF THE INVENTION

This invention relates to a method of producing as the major matabolite long-chain alpha-hydroxyalkanoic acids from an alpha olefin (1-alkene) having from 10 to 18 carbon atoms by cultivating an adapted microorganism of the *Candida lipolytica* species in an aqueous nutrient medium containing the alpha olefin as the carbon source.

It is known that when a strain of *Candida lipolytica* is cultivated in a medium containing an alpha olefin, the yeast can assimilate the alpha olefin with the formation of many metabolites in the culture broth. For example, M. J. Klug et al, *Biotechnology and Bioengineering*, Vol. XI, Number 3 pages 427–440 (1969) disclose that when *Candida lipolytica*, strain Phaff, wash grown in a medium containing 1.0% of 1-hexadecene as the sole carbon source, various oxidative intermediates were formed and identified including 1,2-hexadencanediol, 2-hydroxy-hexadecanoic acid, 15-hexadecen-1-ol, 15-hexadecen-2-ol, 15-hexadecenoic acid, 1,2-expoxy-hexadecane, 9, 17-octadecadienoic acid, etc.

SUMMARY OF THE INVENTION

It has now been found that a microorganism of the *Candida lipolytica* species, which itself is known to assimilate n-paraffins as a carbon source in an aqueous nutrient medium under aerobic conditions, can be adapted to produce more selectively and in higher yields long-chain alpha-hydroxyalkanoic acids as the major metabolite of the assimilation of alpha olefins having from 10 to 18 carbon atoms. The resulting alpha-hydroxyalkanoic acids have the same number of carbon atoms as the alpha olefin precursor.

In the adaptation procedure, the microorganism is first cultivated in an aqueous nutrient medium containing as the carbon source, one or more hydrocarbons boiling in the kerosene range to obtain a culture of the microorganism, then cultivating the resulting culture in a second separate aqueous nutrient medium containing an alpha olefin having from 10 to 18 carbon atoms as the carbon source to obtain a second separate microorganism culture, then repeating a series of separate successive cultivation steps in aqueous nutrient media each containing the above alpha olefin as the carbon source, starting with the above second separate microorganism culture as inoculum the first of the in succeeding cultivation steps and using as inoculum in succeeding cultivation steps the microorganism culture obtained in the next preceding cultivation step. The above repetitive culturing is continued until the microorganism culture is capable of assimilating the alpha olefin to produce as the major metabolite thereof the desired alpha-hydroxyalkanoic acid. The resulting culture is used as inoculum in a final cultivation in an aqueous nitrient medium containing an alpha olefin having from 10 to 18 carbon atoms and there is recovered from the culture broth as the major metabolite of the alpha olefin an alpha-hydroxyalkanoic acid having the same number of carbon atoms as the alpha olefin.

All the above cultivations are conducted under aerobic conditions.

As shown in U.S. Pat. No. 3,492,325, the product acids or esters thereof have such uses as oil-soluble metal complexing agents, emulsifiers, plasticizers for vinyl polymers, lubricant additives etc.

DETAILED DESCRIPTION

The alpha olefins used in the present invention have from 10 to 18 carbon atoms. Such materials are available commercially and can be obtained, for example, by the telomerization of ethylene in the presence of triethylaluminum. Alpha olefins having less than 10 carbon atoms are unsuitable for the economical production of alpha-hydroxyalkanoic acids because of their relatively high volatility, whereas alpha olefins having more than 18 carbon atoms are solids which are poorly dispersible in the nutrient medium and, therefore, are also unsuitable.

The *Candida lipolytica* species employed in the invention are themselves well known and publicly available, and are known to assimilate n-paraffins as the carbon source in an aqueous nutrient medium under aerobic conditions. A suitable strain as described in J. Lodder, "The Yeast", 1971, pages 992–993, has the following properties:

Microscopic observations

The microorganism grows well in an aqueous medium of glucose-yeast extract-peptone. Cultivation at 25° C. for 3 days may cause the yeast to grow into oval or elongate forms. The oval cells have dimensions of 3 to 5 microns by 5 to 11 microns, while the elongate cell measure up to 20 microns and form a membrane. A strain subjected to streak culture in the above medium for a period of one month produces a culture having a cream-colored, delicately-wrinkled, moist appearance with considerable stability. In cultivating the strain on cornmeal agar by the Dalmau plate technique, large amounts of pseudomycelia and true, septate mycelia are formed On the edges or pleura of the mycelia and pseudomycelia, single or paired blastospores are formed.

| Physiological observations: | | | |
|---|---|---|---|
| Fermentivity — negative | | | |
| The carbon utilizing ability is as follows: | | | |
| glucose | + | D-ribose | — |
| Galactose | — | L-rhamnose | — |
| L-sorbose | + or very poor or — | ethanol | + |
| sucrose | — | glycerol | + |
| maltose | — | erythritol | + |
| cellobiose | — | ribitol | — |
| trehalose | — | galactitol | — |
| lactose | — | D-mannitol | + or very poor |
| Melibiose | — | D-glucitol | — |
| raffinose | — | alpha-methyl-D-glucoside | — |
| melezitose | — | salicin | — |
| inulin | — | DL-lactic acid | + |
| soluble starch | — | succinic acid | + or very poor |
| D-xylose | — | citric acid | + |
| L-arabinose | — | inositol | — |
| D-arabinose | — | | |
| Assimilation of potassium nitrate — negative. | | | |
| Growth in a medium containing no vitamins — low. | | | |
| Growth accelerating vitamin — Thiamine. | | | |
| Resistance to common salt — 10 to 14% (w/v). | | | |
| Maximum growth temperature — 33° to 37° C. | | | |

A species of *Candida lipolytica* useful in this invention has been deposited at the Fermentation Research Institute, Agency of Industrial Science and Technology, Chiba, Japan under Deposit No. FERM P-3290 and at American Type Culture Collection, Rockville, Maryland, under Deposit No. 20496.

As has been indicated earlier, the selected *Candida lipolytica* species is adapted to assimilate alpha olefins in such a way as to produce as the major metabolite of such assimilation in alpha-hydroxyalkanoic having the same number of carbon atoms as the assimilated alpha olefin. The first step in such adaptation is to prepare a culture of the *Candida lipolytica* in an aqueous nutrient medium containing as the carbon source one or more hydrocarbons boiling in the kerosene range. For reasons of economy, the mixture of hydrocarbons found in the kerosene, i.e., kerosene itself, is usually and preferably employed. A suitable kerosene, for example, is one having a boiling range of 180° to 230° C. Thereafter, the microorganism culture obtained or a portion thereof is used as inoculum in a second separate cultivation in an aqueous nutrient medium, with one of the selected alpha olefins being substituted for the kerosene boiling range hydrocarbon as the carbon source, to obtain a second separate microorganism culture. The above cultivation step using an alpha olefin as the carbon source is repeated several times in separate successive cultivation steps in an aqueous nutrient medium, starting with the above second separate microorganism culture or a portion thereof as inoculum in the first of the successive cultivation steps and using an inoculum in succeeding cultivation steps the microorganism culture or a portion thereof obtained in the next preceding cultivation step.

Usually, four separate successive cultivation steps using the alpha olefin as the carbon source will be sufficient to confer on the microorganism the ability to produce an alpha-hydroxyalkanoic acid as the major metabolite of alpha olefin assimilation. However, as will be apparent to those skilled in the art, more or less than four such steps may be employed, depending on when the microorganism culture acquires the desired assimilatory ability. The number of repetitive cultivations required can therefore readily be ascertained by one skilled in the art by determining the amount of alpha-hydroxyalkanoic acid obtained in each successive cultivation step and discontinuing the successive cultivations as soon as such acid becomes the major metabolite.

After the adapted microorganism has attained the desired alpha olefin assimilatory capacity, it is used as inoculum in a final cultivation in an aqueous nitrient medium containing a selected alpha olefin. Although more than one alpha olefin can be employed it is usually desirable to use a single alpha olefin in order to obtain a single alpha-hydroxyalkanoic acid and thereby avoid product separation and purification problems. However, if commercial use of the product does not require a single product acid, mixtures of alpha olefins within the indicated carbon number range can be employed.

In the final cultivation, it has been noted that after about 60 hours almost all of the alpha olefin has been metabolized. After about 72 hours, the accumulation of alpha-hydroxyalkanoic acid (product acid) reaches a maximum. When cultivation is continued beyond 72 hours, the product acid begins to disappear. Ordinarily, therefore, cultivation is not continued beyond 72 hours. Yields of about 60% by weight of the product acid, based on the alpha olefin, have been obtained.

In the adaption cultivations and in the final cultivation, the aqueous nutrient medium employed can be any suitable medium promoting growth of the microorganism. One such medium successfully employed contains urea, ammonium sulfate, disodium hydrogen phosphate, monopotassium hydrogen phosphate, ferric chloride, magnesium sulfate, sodium chloride, yeast extract and malt extract, all dissolved in distilled water. All cultivations are conducted aerobically, either in shake flasks or in fermentors. The cultivations are conducted at temperatures in the range 25° to 35° C., preferably at about 30° C. As has been noted, the optimum cultivation time is about 72 hours.

It should be noted that, after being used in the final cultivation, the adapted microorganism decreases in its effectiveness to metabolize alpha olefins to alpha-hydroxyalkanoic acids. It is therefore necessary to perform the herein described adaptation procedure each time it is desired to produce such acids from alpha olefins.

DESCRIPTION OF PREFERRED EMBODIMENT

The present invention will now be described specifically with reference to a preferred embodiment which should not be construed as limiting the spirit and scope of the invention.

EXAMPLE

There is first prepared a basal nutrient medium which is used in the adaptation cultivation and in the final cultivation to obtain the desired alpha-hydroxyalkanoic acid. The basal medium is prepared by dissolving in 1 liter of distilled water the indicated amounts of the following compounds:

| | |
|---|---|
| $(NH_2)_2CO$ | 2.0g |
| $(NH_4)_2SO_4$ | 2.2g |
| $Na_2HPO_4 \cdot 12H_2O$ | 3.0g |
| $KH_2PO_4$ | 1.5g |
| $FeCl_3 \cdot 6H_2O$ | 0.01g |
| $MgSO_4 \cdot 7H_2O$ | 0.5g |
| NaCl | 0.5g |
| Yeast extract | 0.2g |
| Malt extract | 0.2g |

Adaptation of Candida lipolytica

Step 1. To one liter of the above basal medium in a shake flask there was added 100 ml of kerosene having a boiling range of 180° to 230° C., and the resulting mixture was sterilized. The sterilized mixture was then inoculated with two platinum loopfuls of a culture of *Candida lipolytica* ATCC 20496 from a malt extract agar slant. The mixture was then cultured on a reciprocal shaker at 110 oscillations per minute (65 mm amplitude) at 30° C. for 4 days.

Step 2. To a separate one liter portion of the above basal medium in a shake flask there was added 100 ml of 1-decene. The mixture was sterilized, inoculated with 5 ml of the culture obtained in Step 1, and then cultured under the identical conditions set forth in Step 1.

Step 3. To another separate one liter portion of the above basal medium in a shake flask, there was added 50 ml of 1-decene. The mixture was sterilized, inoculated with 5 ml of the culture obtained in Step 2, and then cultured under the identical conditions set forth in Step 1.

Step 4. To still another separate one liter portion of the above basal medium in a shake flask, there was added 20 ml of 1-decene. The mixture was sterilized, inoculated with 5 ml of the culture obtained in Step 3, and then cultured under the identical conditions set forth in Step 1.

Step 5. To yet another separate one liter portion of the above basal medium, there was added 20 ml of 1-decene. The mixture was sterilized, inoculated with 5 ml of the culture obtained in Step 4, and then cultured under the identical conditions set forth in Step 1. In order to obtain a pure culture isolate, one platinum loop of the resulting culture was transferred to a nutrient agar medium in a Petri dish, a sheet of filter paper soaked in 1-decene was placed on the inoculated agar which was then incubated at 30° C. for 72 hours to form a colony of the microorganism.

Final Cultivation. To a separate one liter portion of the above basal medium, there was added 10 ml of 1-decene. The mixture was sterilized, inoculated with one platinum loopful of microorganism cells from the pure culture colony obtained in Step 5 and cultured on a reciprocal shaker under conditions identical to those in Step 1, except that the temperature was 30° ± 3° C. and cultivation was stopped after 60 hours. The culture was removed from the flask, the yeast cells were separated from the broth, and the remaining broth was extracted with ether. After evaporating the ether from the extract, there was obtained 6.2 g. of crystalline alpha-hydroxydecanoic acid having a purity of 95 percent. The yield of alpha-hydroxydecanoic acid, based on the 1-decene, was approximately 62 mol percent.

For purposes of comparison, when the above final cultivation was repeated with an identical strain of *Candida lipolytica* which had not been subjected to the herein described adaptation procedure, growth of the strain was poor even after 72 hours and unreacted 1-decene remained in the broth with no observable production of alpha-hydroxydecanoic acid.

In the above detailed example, the isolation of a pure culture of the adapted microorganism and use of the pure culture in the final cultivation is shown. The use of such a pure culture is unnecessary for the production of alpha-hydroxyalkanoic acids in accordance with the invention. The culture obtained in the final adaptation cultivation step, or a portion thereof, is successfully employed as inoculum in the final cultivation step to obtain the acids.

What is claimed is:

1. A method of producing a long-chain alpha-hydroxyalkanoic acid from an alpha olefin having from 10 to 18 carbon atoms which comprises:
   a. adapting a microorganism of the *Candida lipolytica* species to assimilate said alpha olefin and to produce said acid as the major metabolite of said assimilation by
      1. first cultivating said microorganism in an aqueous nutrient medium containing a hydrocarbon boiling in the kerosene range to obtain a culture of said microorganism,
      2. then cultivating said culture in a second separate aqueous nutrient medium containing an alpha having from 10 to 18 carbon atoms to obtain a second separate microorganism culture,
      3. repeating in separate successive cultivation steps the cultivation of step (2), starting with said second separate microorganism culture as inoculum in the first of the successive cultivation steps and utilizing as inoculum in succeeding cultivation steps the microorganism culture obtained in the next preceding cultivation step, until there is obtained a final microorganism culture capable of producing said acid as the major metabolite of said alpha olefin assimilation;
   b. then cultivating in an aqueous nutrient medium containing an alpha olefin having from 10 to 18 carbons said final microorganism culture from step(a)(3); and
   c. recovering from cultivation step(b) an alphahydroxycarboxylic acid having the same number of carbon atoms as said alpha olefin.

2. The method of claim 1, wherein the cultivation of step (b) does not exceed 72 hours.

3. The method of claim 2, wherein the microorganism of step (a)(1) in *Candida lipolytica* ATCC 20496.

* * * * *

UNITED STATES PATENT AND TRADEMARK OFFICE
CERTIFICATE OF CORRECTION

PATENT NO. : 4,059,488
DATED : November 22, 1977
INVENTOR(S) : Kazumasa Hachikubo and Shuzo Suzuki It is certified that error appears in the above-identified patent and that said Letters Patent are hereby corrected as shown below:

At Column 1, line 51 after the word "inoculum" insert the word --in--.

At Column 1, line 51 delete the words "in succeeding" and replace with --successive--.

At Column 6, line 16 after the word "alpha" insert the word --olefin--.

At Column 6, line 39 delete the word "in" and replace with the word --is--.

Signed and Sealed this

Eleventh Day of April 1978

[SEAL]

Attest:

RUTH C. MASON
Attesting Officer

LUTRELLE F. PARKER
Acting Commissioner of Patents and Trademarks